(12) United States Patent
Cheng et al.

(10) Patent No.: US 8,896,032 B2
(45) Date of Patent: Nov. 25, 2014

(54) SELF-ALIGNED BIOSENSORS WITH ENHANCED SENSITIVITY

(71) Applicant: International Business Machines Corporation, Armonk, NY (US)

(72) Inventors: Kangguo Cheng, Schenectady, NY (US); Bruce B. Doris, Brewster, NY (US); Ali Khakifirooz, Mountain View, NY (US); Raghavasimhan Sreenivasan, Schenectady, NY (US); Sufi Zafar, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/748,197

(22) Filed: Jan. 23, 2013

(65) Prior Publication Data

US 2014/0203332 A1    Jul. 24, 2014

(51) Int. Cl.
*G01N 27/414* (2006.01)
*H01L 29/66* (2006.01)

(52) U.S. Cl.
CPC .......... *H01L 29/66* (2013.01); *H01L 29/66075* (2013.01)
USPC ....................................................... 257/253

(58) Field of Classification Search
CPC ................................................... G01N 27/414
USPC ......... 438/49; 204/601–605, 607, 628, 403.1; 205/775; 257/253
See application file for complete search history.

(56) References Cited

U.S. PATENT DOCUMENTS

| | | | |
|---|---|---|---|
| 5,393,401 A * | 2/1995 | Knoll | 204/403.06 |
| 7,329,387 B2 | 2/2008 | Fukutani et al. | |
| 8,080,152 B2 | 12/2011 | Sirringhaus | |
| 8,154,058 B2 | 4/2012 | Hwang et al. | |
| 2006/0272942 A1 * | 12/2006 | Sirringhaus | 204/406 |
| 2007/0007133 A1 | 1/2007 | Mang et al. | |
| 2010/0065892 A1 | 3/2010 | Hwang et al. | |
| 2011/0180427 A1 | 7/2011 | Matsumoto et al. | |
| 2012/0132991 A1 * | 5/2012 | Kuzumoto et al. | 257/347 |

FOREIGN PATENT DOCUMENTS

KR       100964202       8/2009

OTHER PUBLICATIONS

Notice of Allowance dated Nov. 8, 2013 received in a related U.S. Patent Application, namely U.S. Appl. No. 14/010,034.
Stern, E., et al., "Label-free immunodetection with CMOS-compatible semiconducting nanowires", Nature, Feb. 1, 2007, vol. 445.

(Continued)

*Primary Examiner* — Olik Chaudhuri
*Assistant Examiner* — Christine Enad
(74) *Attorney, Agent, or Firm* — Scully, Scott, Murphy & Presser, P.C.; Louis J. Percello, Esq.

(57) ABSTRACT

Non-planar semiconductor FET based sensors are provided that have an enhanced sensing area to volume ratio which results in faster response times than existing planar FET based sensors. The FET based sensors of the present disclosure include a V-shaped gate dielectric portion located in a V-shaped opening formed in a semiconductor substrate. In some embodiments, the FET based sensors of the present disclosure also include a self-aligned source region and a self-aligned drain region located in the semiconductor substrate and on opposing sides of the V-shaped opening. In other embodiments, the FET based sensors include a self-aligned source region and a self-aligned drain region located in the semiconductor substrate and on opposing sides of a gate dielectric material portion that is present on an uppermost surface of the semiconductor substrate.

16 Claims, 9 Drawing Sheets

(56) References Cited

OTHER PUBLICATIONS

Bergveld, P., "Thirty years of ISFETOLOGY What happened in the past 30 years and what may happen in the next 30 years", Sensors and Actuators B, Jan. 2003, 88, 1-20.

Zafar, S., et al., "Optimization of pH sensing using silicon nanowire field effect transistors with $HfO_2$ as the sensing surface", Nanotechnology, Sep. 2011, 22, 405501 (6pp).

* cited by examiner

SELF-ALIGNED BIOSENSORS WITH ENHANCED SENSITIVITY

BACKGROUND

The present disclosure relates to semiconductor structures and methods of forming the same. More particularly, the present disclosure relates to semiconductor based field effect transistors (FETs) which can be used as biosensors and methods of forming the same.

A biomolecule is any molecule that is produced by a living organism, including large macromolecules such as proteins, polysaccharides, lipids, and nucleic acids, as well as small molecules such as primary metabolites, secondary metabolites, and natural products. Detection of biomolecules such as, for example, proteins and viruses play an important role in healthcare and drug discovery.

Traditionally, biomolecules are detected using florescene or isotope labeling and patch clamp. These traditional biomolecule detection methods have limited sensitivity and automation. Also, the traditional biomolecule detection methods exhibit slow response time and require large amounts of reagent, which may not always be available.

Recently, field effect transistor (FET) sensors have been proposed for biosensing. Most FET based sensors are planar and provide improved biosensing capabilities over their traditionally used biomolecule detection methods. In a typical planar FET based sensor, the sensor is used for sensing charged molecules or ions, which cause a change in the drain current of the planar FET sensor when the charged species are brought into proximity with the channel region of the FET sensor.

Despite providing improved biosensing capability over the traditional biomolecule detection methods mentioned above, there is a need for further improvements within FET based sensors. In particular, there is a need for providing FET based sensors which have a high sensing area to volume ratio, while maintaining the density of traditional FET devices.

SUMMARY

Non-planar semiconductor FET based sensors are provided that have an enhanced sensing area to volume ratio which results in faster response times than existing planar FET based sensors. The FET based sensors of the present disclosure include a V-shaped gate dielectric portion located in a V-shaped opening formed in a semiconductor substrate. In some embodiments, the FET based sensors of the present disclosure also include a self-aligned source region and a self-aligned drain region located in the semiconductor substrate and on opposing sides of the V-shaped opening. In other embodiments, the FET based sensors include a self-aligned source region and a self-aligned drain region located in the semiconductor substrate and on opposing sides of a gate dielectric material portion that is present on an uppermost surface of the semiconductor substrate.

In one aspect of the present disclosure, a semiconductor structure, i.e., semiconductor based FET sensor, is provided that is capable of sensing biomolecules. In one embodiment, the semiconductor structure of the present disclosure includes a semiconductor substrate having a V-shaped opening located therein. The V-shaped opening within the semiconductor substrate exposes surfaces of the semiconductor substrate that are located beneath an uppermost surface of the semiconductor substrate. A gate dielectric having a bare uppermost surface is located on the exposed surfaces of the semiconductor substrate within the V-shaped opening. A source region is located in a portion of the uppermost surface of the semiconductor substrate and positioned adjacent one side of the V-shaped opening. A drain region is located in another portion of the uppermost surface of the semiconductor substrate and positioned adjacent an opposite side of the V-shaped opening.

In another embodiment, the semiconductor structure of the present disclosure includes a semiconductor substrate having a V-shaped opening located therein. The V-shaped opening within the semiconductor substrate exposes surfaces of the semiconductor substrate that are located beneath an uppermost surface of the semiconductor substrate. A gate dielectric having a bare uppermost surface is located on a portion of the exposed uppermost surface of the semiconductor substrate and on the exposed surfaces of the semiconductor substrate within a portion of the V-shaped opening. A source region is located in an exposed portion of the uppermost surface of the semiconductor substrate and positioned on one side of the gate dielectric. A drain region is located in another exposed portion of the uppermost surface of semiconductor substrate and positioned on another side of the gate dielectric.

In another aspect of the present disclosure, a method of forming a semiconductor structure that is capable of sensing biomolecules is provided. In accordance with one embodiment of this aspect of the present disclosure, the method includes forming a blanket layer of a hard mask material on an uppermost surface of a semiconductor substrate. The blanket layer of hard mask material is then patterned providing a first hard mask portion and a second hard mask portion on the uppermost surface of the semiconductor substrate, wherein a portion of the uppermost surface of the semiconductor substrate is exposed. The exposed portion of the uppermost surface of the semiconductor substrate is then etched providing a V-shaped opening within the semiconductor substrate and exposing surfaces of the semiconductor substrate that are located beneath the uppermost surface of the semiconductor substrate. Next, a gate dielectric is formed on a sidewall surface of each hard mask portion and on the exposed surfaces of the semiconductor substrate within the V-shaped opening, and thereafter a sacrificial gate material is formed on the gate dielectric. The first and second hard mask portions are then removed exposing portions of the uppermost surface of the semiconductor substrate that are located adjacent the V-shaped opening. Next, a source region is formed in one of the exposed portions of the semiconductor substrate and a drain region is formed in another of the exposed portions of the semiconductor substrate. A first insulator cap portion is formed atop the source region and a second insulator cap portion is formed atop the drain region. Next, an entirety of the sacrificial gate material is removed from the structure.

In accordance with another embodiment of the present disclosure, the method includes forming a blanket layer of a hard mask material on an uppermost surface of a semiconductor substrate. The blanket layer of hard mask material is then patterned providing a first hard mask portion and a second hard mask portion on the uppermost surface of the semiconductor substrate, wherein a portion of the uppermost surface of the semiconductor substrate is exposed. The exposed portion of the uppermost surface of the semiconductor substrate is then etched providing a V-shaped opening within the semiconductor substrate and exposing surfaces of the semiconductor substrate that are located beneath the uppermost surface of the semiconductor substrate. The first and second hard mask portions are then removed exposing portions of the uppermost surface of the semiconductor substrate that are located adjacent the V-shaped opening. Next, a patterned structure including, from bottom to top, a gate dielectric and a sacrificial gate material is formed on portions of the exposed uppermost surface of the semiconductor substrate and on the exposed surfaces of the semiconductor substrate within the V-shaped opening. Next, a source region is formed in the exposed portions of the uppermost surface of the semiconductor substrate on one side of the patterned structure and a drain region is formed in another exposed portion of the uppermost surface of the semiconductor substrate on another side of the patterned structure. Next, an entirety of the sacrificial gate material is removed from the structure.

DETAILED DESCRIPTION

The present disclosure will now be described in greater detail by referring to the following discussion and drawings that accompany the present application. It is noted that the drawings of the present application are provided for illustrative purposes only and, as such, the drawings are not drawn to scale. In the following description, numerous specific details are set forth, such as particular structures, components, materials, dimensions, processing steps and techniques, in order to provide a thorough understanding of the present disclosure. However, it will be appreciated by one of ordinary skill in the art that the present disclosure may be practiced without these specific details. In other instances, well-known structures or processing steps have not been described in detail in order to avoid obscuring the present disclosure.

It will be understood that when an element as a layer, region or substrate is referred to as being "on" or "over" another element, it can be directly on the other element or intervening elements may also be present. In contrast, when an element is referred to as being "directly on" or "directly over" another element, there are no intervening elements present.

As stated above, the present disclosure provides non-planar semiconductor FET based sensors that have an enhanced sensing area to volume ratio which results in faster response times than existing planar FET based sensors. The FET based sensors of the present disclosure include a V-shaped gate dielectric portion located in a V-shaped opening formed in a semiconductor substrate. In some embodiments (such as will be shown in FIGS. 1-12), the FET based sensors of the present disclosure also include a self-aligned source region and a self-aligned drain region located in the semiconductor substrate and on opposing sides of the V-shaped opening. In other embodiments (such as will be shown in FIGS. 13-16), the FET based sensors include a self-aligned source region and a self-aligned drain region located in the semiconductor substrate and on opposing sides of a gate dielectric material portion that is present on an uppermost surface of the semiconductor substrate.

Notwithstanding which embodiment of the present disclosure is employed, non-planar semiconductor FET based sensors are provided that exhibit a fast response time due to the large sensing area provided by employing a semiconductor substrate having a V-shaped opening it which the V-shaped gate dielectric portion that is used for biosensing is housed. Also, the non-planar semiconductor FET based sensors of the present disclosure can be formed at a low cost since standard semiconductor processing is employed in the present disclosure in forming the same.

Figure 1:
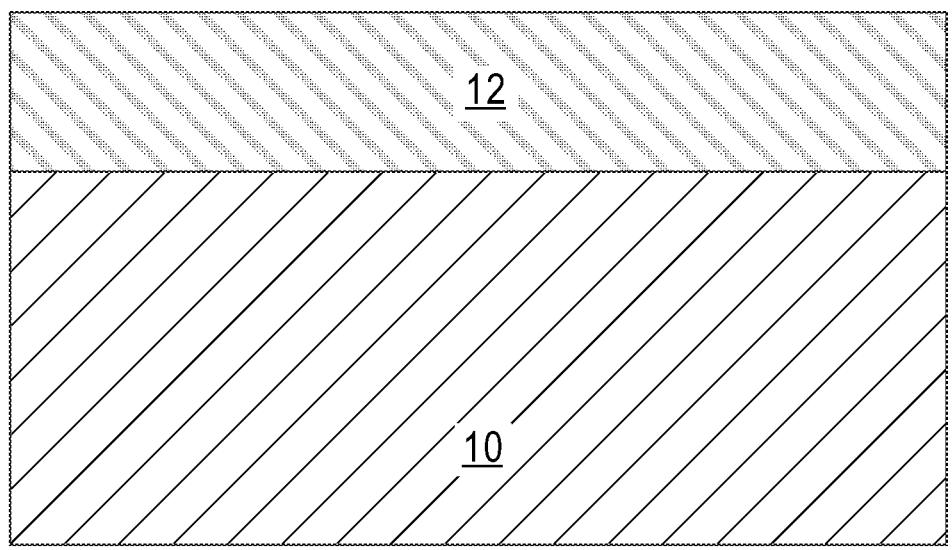
FIG. 1 is a pictorial representation (through a cross sectional view) illustrating an initial structure including a semiconductor substrate having a blanket layer of hard mask material located on an uppermost surface thereof that can be employed in one embodiment of the present disclosure.

Referring to FIG. 1, there is illustrated an initial structure that can be employed in one embodiment of the present disclosure. The initial structure shown in FIG. 1 includes a semiconductor substrate 10 having a blanket layer of hard mask material 12 located on an uppermost surface thereof.

The semiconductor substrate 10 that can be employed in the present disclosure includes a semiconductor material such as, but not limited to, Si, Ge, SiGe, SiGeC, SiC, GaAs, InAs, InP and other III/V or II/VI compound semiconductors. The semiconductor substrate 10 may also include a layered substrate such as, for example, Si/SiGe, Si/Ge, and Si/SiC. In some embodiments of the present disclosure, the semiconductor substrate 10 may include a semiconductor-on-insulator substrate such as, for example, silicon-on-insulators (SOIs) or silicon germanium-on-insulators (SGOIs). In other embodiments, a semiconductor-on-sapphire substrate can be used as the semiconductor substrate 10.

The semiconductor substrate 10 can be undoped, have a homogeneous doping of p-type or n-type, or can have a plurality of doped semiconductor portions having different dopant concentrations and/or different conductivity types (i.e., p-type or n-type). In one embodiment, the semiconductor substrate 10 can be a bulk single crystalline semiconductor substrate including at least one doped or undoped semiconductor material throughout the entirety thereof. The thickness of the semiconductor substrate 10 can be from 50 micron to 2 cm, although lesser and greater thicknesses can also be employed in the present disclosure. In one embodiment of the present disclosure, the semiconductor substrate 10 is a bulk single crystalline silicon semiconductor substrate.

After selecting an appropriate semiconductor substrate 10, a blanket layer of hard mask material 12 can be formed directly on an uppermost surface of the semiconductor substrate 10. The blanket layer of hard mask 12 is a continuous layer that covers the entirety of the uppermost surface of the semiconductor substrate 10. The blanket layer of hard mask material 12 can include, but is not limited to, an oxide, a nitride, an oxynitride or any multilayered combination thereof. In one embodiment, the hard mask material is an oxide such as silicon oxide, while in another embodiment the hard mask material is a nitride such as silicon nitride. The blanket layer of hard mask material 12 can be formed utilizing a conventional deposition process including, for example, chemical vapor deposition (CVD), plasma enhanced chemical vapor deposition (PECVD), chemical solution deposition, evaporation, and physical vapor deposition (PVD). Alternatively, the blanket layer of hard mask material 12 can be formed by one of thermal oxidation, and thermal nitridation. In one embodiment of the present disclosure, the thickness of the blanket layer of hard mask material 12 can be from 5 nm to 100 nm. In other embodiments, other thicknesses that are greater than or lesser than the thickness range mentioned above can also be employed for the blanket layer of hard mask material 12.

Figure 2:
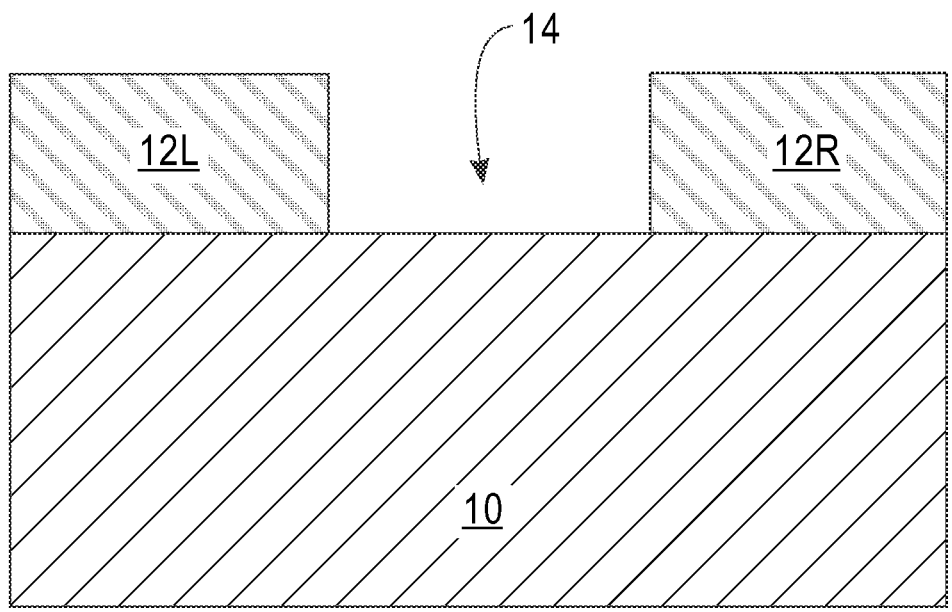
FIG. 2 is a pictorial representation (through a cross sectional view) illustrating the initial structure of FIG. 1 after patterning the blanket layer of hard mask material to include at least one opening therein that exposes a portion of the uppermost surface of the semiconductor substrate.

Referring now to FIG. 2, there is illustrated the initial structure of FIG. 1 after patterning the blanket layer of hard mask material 12 to include at least one opening 14 therein that exposes a portion of the uppermost surface of the semiconductor substrate 10. Although a single opening 14 is described and illustrated, a plurality of such openings can be formed in the blanket layer of hard mask material 12. The remaining portions of the blanket layer of hard mask material 12 can be referred to herein as a first hard mask material portion 12L and a second hard mask material portion 12R. The remaining portions of the blanket layer of hard mask material 12L, 12R are used as an etch mask during an etching process to be subsequently performed.

The patterning of the blanket layer of hard mask material 12 can performed by lithography and etching. The lithographic process can include forming a photoresist (not shown) atop the blanket layer of hard mask material 12, exposing the photoresist to a desired pattern of radiation and developing the exposed photoresist utilizing a conventional resist developer. The pattern in the photoresist is then transferred into the underlying blanket layer of hard mask material 12 by etching. The etching can include a dry etching process (such as, for example, reactive ion etching, ion beam etching, plasma etching or laser ablation), and/or a wet chemical etching process. Typically, reactive ion etching is used to transfer the pattern from the developed photoresist into the blanket layer of hard mask material 12. After patterning the underlying blanket layer of hard mask material 12, the patterned photoresist can be removed utilizing a conventional stripping process such as, for example, ashing.

Figure 3:
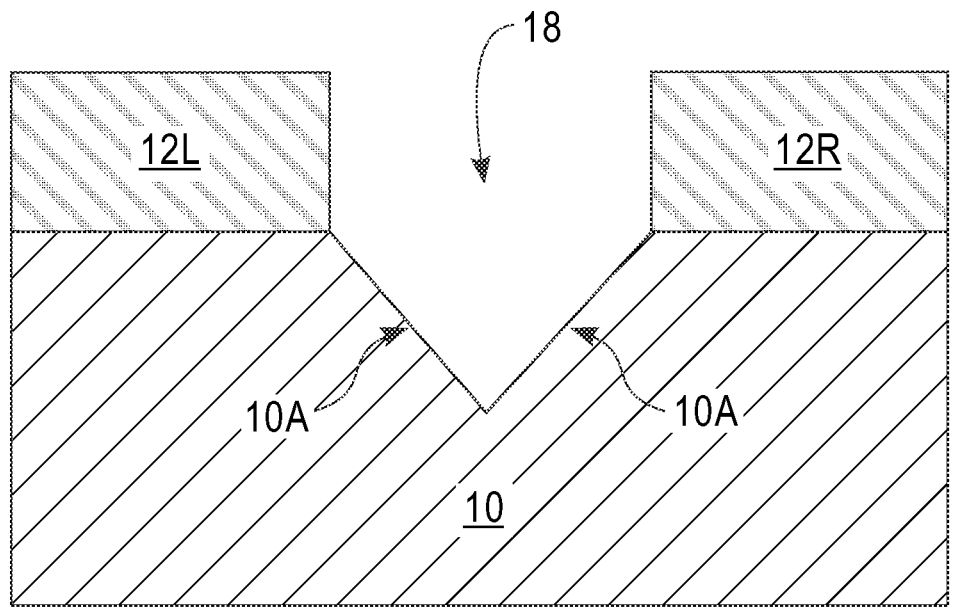
FIG. 3 is a pictorial representation (through a cross sectional view) illustrating the structure of FIG. 2 after performing a crystallographic wet etch.

Referring now to FIG. 3, there is illustrated the structure of FIG. 2 after performing a crystallographic wet etch using the remaining portions of the blanket layer of hard mask material 12L, 12R as an etch mask; the crystallographic wet etch may also be referred to as an anisotropic wet etch that is orientation dependent. The crystallographic wet etch provides a V-shaped opening 18 within the semiconductor substrate 10 that exposes surfaces 10A of the semiconductor substrate 10 that are located beneath the uppermost surface of the semiconductor substrate 10. The term "V-shaped opening" is used in the present disclosure to describe an opening that is formed into the substrate 10 having two non-vertical walls defined by the exposed surfaces 10A and an apex defined at the intersection of the two exposed surfaces 10A. The exposed surfaces 10A of semiconductor substrate 10 have a different crystal orientation as that of the uppermost surface of the semiconductor substrate 10. For example, and when silicon having a (100) surface crystallographic orientation is employed as the semiconductor substrate 10, the crystallographic wet etch exposes surfaces 10A of the silicon substrate that are within a (111) crystal plane.

In one embodiment of the present disclosure, the crystallographic wet etch that is employed includes using KOH as a chemical etchant. In another embodiment of the present disclosure, the crystallographic wet etch that is employed includes using an aqueous solution of ethylene diamine and pyrocatechol as a chemical etchant. In yet another embodiment, the crystallographic wet etch that is employed includes using an aqueous solution of tetramethylammonium hydroxide as a chemical etchant. In yet another embodiment, the crystallographic wet etch that is employed includes using an aqueous solution of ammonia as a chemical etchant.

Figure 4:
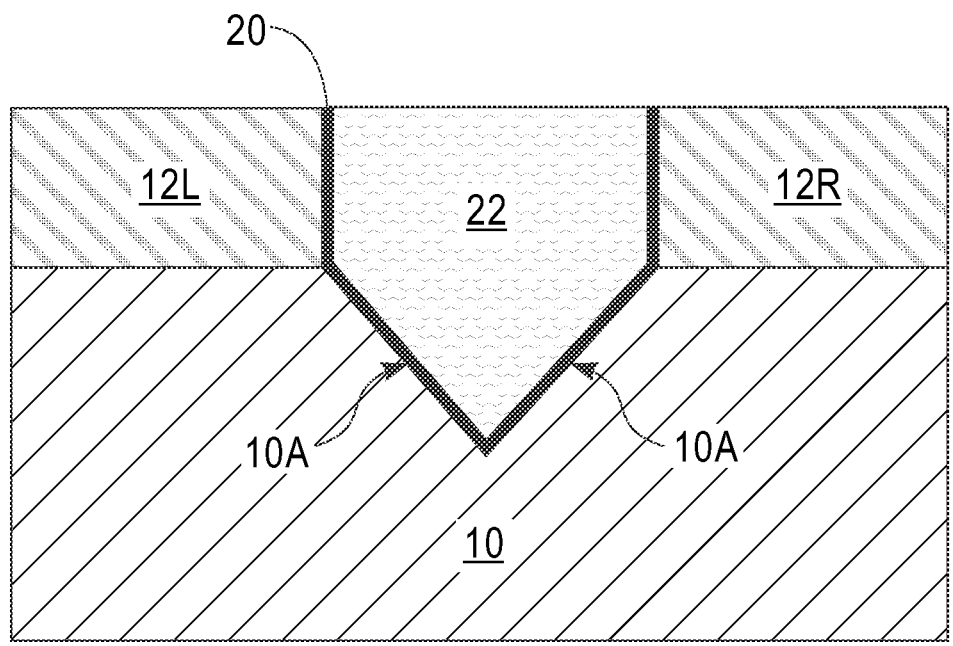
FIG. 4 is a pictorial representation (through a cross sectional view) illustrating the structure of FIG. 3 after forming a gate dielectric, a sacrificial gate material, and planarization.

Referring now to FIG. 4, there is illustrated the structure of FIG. 3 after forming a gate dielectric 20, a sacrificial gate material 22, and planarization. Prior to planarization, the gate dielectric 20 can be on a sidewall surface of each remaining portion of the blanket layer of hard mask material 12L, 12R, on the exposed surfaces 10A of the semiconductor substrate 10 and on the uppermost surface of each remaining hard mask material portion 12L, 12R. After planarization, the gate dielectric 20 is still present on the sidewall surface of each remaining hard mask material portion 12L, 12R, and on the exposed surfaces 10A of the semiconductor substrate 10, but not on the uppermost surface of each remaining hard mask material portion 12L, 12R. Prior to planarization, the sacrificial gate material 22 can be present on the exposed uppermost surface of the gate dielectric 20 which is present atop and on the sidewalls of each remaining hard mask material portion 12L, 12R, as well as the exposed uppermost surface of the gate dielectric 20 that is present on the exposed surfaces 10A of the semiconductor substrate 10. After planarization, the sacrificial gate material 22 is still present on the sidewalls of each remaining hard mask material portion 12L, 12R, and the exposed uppermost surface of the gate dielectric 20 that is present on the exposed surfaces 10A of the semiconductor substrate 10, but not on the exposed uppermost surface of the gate dielectric 20 which is present atop each remaining hard mask material portion 12L, 12R.

The gate dielectric 20 that can be employed in the present disclosure includes any insulating material such as for example, an organic polymer, an oxide, a nitride, an oxynitride or a multilayered stack thereof. In one embodiment, the gate dielectric 20 can include a semiconductor oxide, a semiconductor nitride or a semiconductor oxynitride. In another embodiment, the gate dielectric 20 can include a dielectric metal oxide or mixed metal oxide having a dielectric constant that is greater than the dielectric constant of silicon oxide, i.e., 3.9. Typically, the dielectric material that can be employed as the gate dielectric 20 has a dielectric constant greater than 4.0, with a dielectric constant of greater than 8.0 being more typical. Such dielectric materials are referred to herein as high k dielectrics. Exemplary high k dielectrics include, but are not limited to, $HfO_2$, $ZrO_2$, $La_2O_3$, $Al_2O_3$, $TiO_2$, $SrTiO_3$, $LaAlO_3$, $Y_2O_3$, $HfO_xN_y$, $ZrO_xN_y$, $La_2O_xN_y$, $Al_2O_xN_y$, $TiO_xN_y$, $SrTiO_xN_y$, $LaAlO_xN_y$, $Y_2O_xN_y$, SiON, $SiN_x$, a silicate thereof, and an alloy thereof. Multilayered stacks of these high k materials can also be employed as the gate dielectric 20. Each value of x is independently from 0.5 to 3 and each value of y is independently from 0 to 2. The thickness of the gate dielectric 20 that can be employed may vary depending on the technique used to form the same. Typically, the gate dielectric 20 that can be employed has a thickness from 1 nm to 20 nm, with a thickness from 2 nm to 10 nm being more typical.

The gate dielectric 20 can be formed by methods well known in the art. In one embodiment, the gate dielectric 20 can be formed by a deposition process such as, for example, chemical vapor deposition (CVD), plasma enhanced chemical vapor deposition (PECVD), physical vapor deposition (PVD), molecular beam deposition (MBD), pulsed laser deposition (PLD), liquid source misted chemical deposition (LSMCD), and atomic layer deposition (ALD).

In one embodiment of the present disclosure, the sacrificial gate material 22 may be composed of a semiconductor-containing material, such as a silicon-containing material. Silicon-containing materials that are suitable for the sacrificial gate material 22 include, but are not limited to, silicon (Si), single crystal silicon, polycrystalline silicon, amorphous silicon, $SiO_2$, $Si_3N_4$, $SiO_xN_y$, SiC, SiCO, SiCOH, and SiCH compounds, and the above-mentioned silicon-containing materials with some or all of the Si replaced by Ge. In one example, the sacrificial gate material 22 can be composed of amorphous silicon. In another embodiment, the sacrificial gate material 22 can be composed of amorphous carbon. In some embodiments, other materials, such as dielectrics and metals, can be employed as the sacrificial gate material 22 so long as the material chosen as the sacrificial gate material 22 can be removed selective to the gate dielectric 20.

The sacrificial gate material 22 may be formed using a deposition process, such as chemical vapor deposition (CVD). Chemical vapor deposition (CVD) is a deposition process in which a deposited species is formed as a result of chemical reaction between gaseous reactants at an elevated temperature (typically being greater than 200° C.), wherein solid product of the reaction is deposited on the surface on which a film, coating, or layer of the solid product is to be formed. Variations of CVD processes include, but not limited to, Atmospheric Pressure CVD (APCVD), Low Pressure CVD (LPCVD) and Plasma Enhanced CVD (PECVD), Metal-Organic CVD (MOCVD) and combinations thereof. The sacrificial gate material 22 may also be deposited using evaporation, chemical solution deposition, spin on deposition, and physical vapor deposition (PVD) methods. The sacrificial gate material 22 generally has a thickness that ensures complete filing of the V-shaped opening 18 up to an beyond the uppermost surface of each hard mask material portion 12L, 12R.

The planarization process that is used in providing the structure shown in FIG. 4 includes chemical mechanical polishing (CMP) and/or grinding. After planarization, the uppermost surfaces of the sacrificial gate material 22 and the gate dielectric 20 are coplanar with the uppermost surface of each remaining hard mask material portion 12L, 12R.

Figure 5:
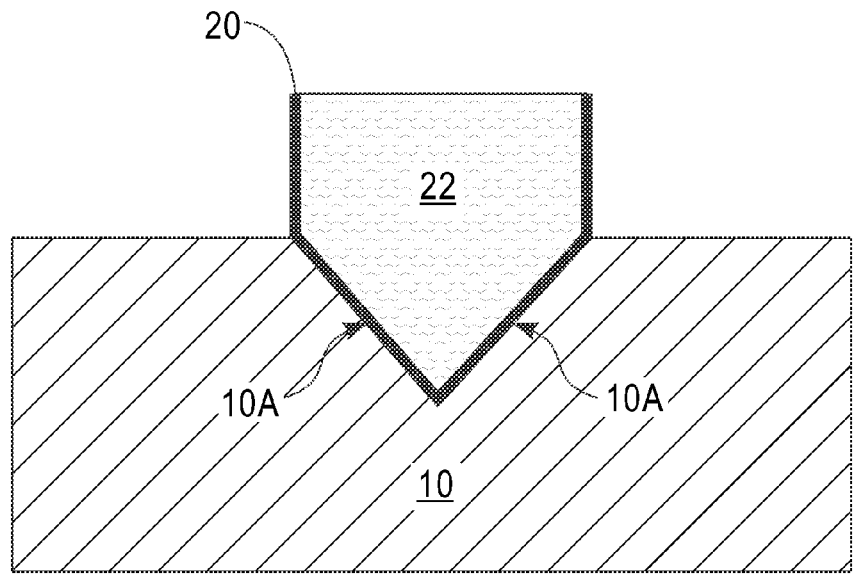
FIG. 5 is a pictorial representation (through a cross sectional view) illustrating the structure of FIG. 4 after removing the remaining hard mask material portions from the structure.

Referring now to FIG. 5, there is depicted the structure of FIG. 4 after removing the remaining hard mask material portions 12L, 12R from the structure. The removal of the remaining hard mask material portions 12L, 12R from the structure exposes portions of the uppermost surface of the semiconductor substrate 10 that are adjacent the V-shaped opening 18 that is now filled with the gate dielectric 20 and the sacrificial gate material 22.

The removal of the remaining hard mask material portions 12L, 12R from the structure includes an etch that selectively removes the remaining hard mask material portions 12L, 12R relative to the gate dielectric 20 and the sacrificial gate material 22. As used herein, the term "selective" in reference to a material removal process denotes that the rate of material removal for a first material is greater than the rate of removal for at least another material of the structure to which the material removal process is being applied. In some examples, the selectivity may be greater than 10:1. In other embodiments, the selectivity may be greater than 100:1.

In one embodiment of the present disclosure, dilute hydrofluoric acid can be used to remove remaining hard mask material portions 12L, 12R from the structure. In another embodiment of the present disclosure, chemical oxide removal (COR) can be used to remove remaining hard mask material portions 12L, 12R from the structure.

Figure 6:
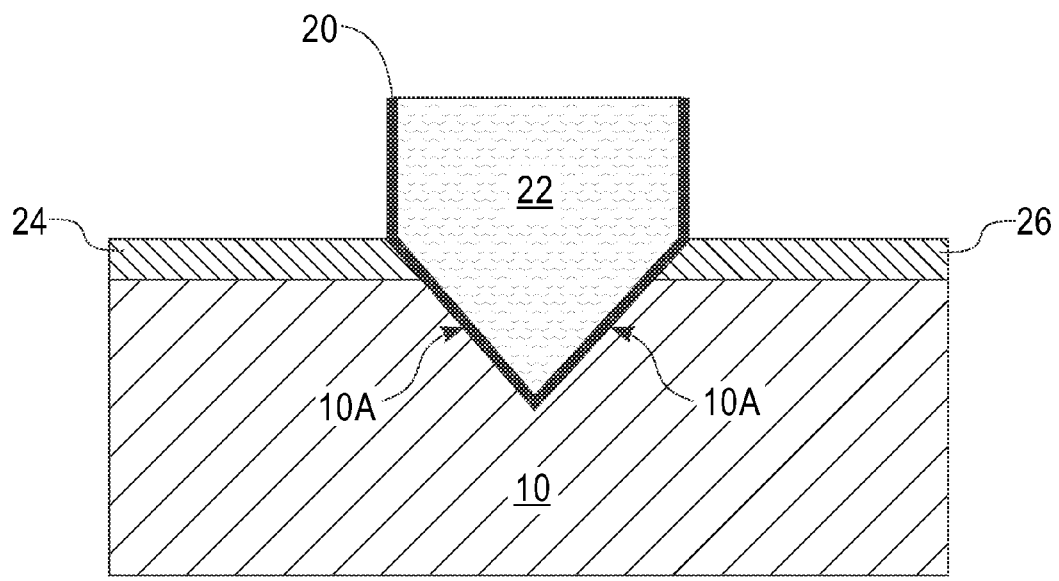
FIG. 6 is a pictorial representation (through a cross sectional view) illustrating the structure of FIG. 5 after forming a source region and a drain region within exposed portions of the semiconductor substrate.

Referring now to FIG. 6, there is illustrated the structure of FIG. 5 after forming a source region 24 and a drain region 26 within exposed portions of the semiconductor substrate 10. The source region 24 is formed adjacent one side of the V-shaped opening 18, while the drain region is formed adjacent another side of the V-shaped opening 18. The source region 24 and the drain region 26 can be formed by one of ion implantation of a dopant, gas phase doping or out-diffusion of a dopant from a sacrificial dopant source material into the exposed portions of the uppermost surface of the semiconductor substrate 10. The dopants that can be used in the present disclosure may be p-type dopants or n-type dopants. As used herein, "p-type" refers to the addition of impurities to an intrinsic semiconductor that creates deficiencies of valence electrons. Examples of p-type dopants include elements from Group IIIA of the Periodic Table of Elements, i.e., boron, aluminum, gallium and indium. As used herein, "n-type" refers to the addition of impurities that contributes free electrons to an intrinsic semiconductor. Examples of n-type dopants include elements from Group VA of the Periodic Table of Elements, i.e., antimony, arsenic and phosphorous. In one embodiment, the concentration of dopant in the source region 24 and the drain region 26 may range from $1 \times 10^{18}$ atoms/cm$^3$ to $2 \times 10^{21}$ atoms/cm$^3$. Other dopant concentrations that are lesser than or greater than the range mentioned above can also be employed in the present disclosure.

The source region 24 and the drain region 26 extend from the uppermost surface of the semiconductor substrate 10 inward into the semiconductor substrate 10. The source region 24 has an edge portion that contacts a portion of the gate dielectric 20 and the drain region 26 has an edge portion that contacts another portion of the gate dielectric 20. In some embodiments, the source region 24 and the drain region 26 extend into the semiconductor substrate 10 to a depth that is equal with or lesser than the depth of the apex of the V-shaped opening 18.

In some embodiments (not shown here), a portion of the gate dielectric 20 that extends above the V-shaped opening 18 can be removed. The removal of the portion of the gate dielectric 20 that extends above the V-shaped opening 18 can be performed either prior to, or after forming the source region 24 and the drain region 26. The removal of the portion of the gate dielectric 20 that extends above the V-shaped opening 18 can be performed utilizing an etching process that selectively removes the portion of the gate dielectric 20 that extends above the V-shaped opening 18 relative to the sacrificial gate material 22. In one embodiment, a reactive ion etch (RIE) comprising $BCl_3$ can be used to remove the portion of the gate dielectric 20 that extends above the V-shaped opening 18. In one embodiment, an aqueous solution containing hydrofluoric acid can be used to remove the portion of the gate dielectric 20 that extends above the V-shaped opening 18.

In some embodiments, a raised source region and a raised drain region (not shown in the present embodiment) can be formed atop the source region 24 and drain region 26, respectively, shown in FIG. 6. As used herein, the term "raised" in combination with source and/or drain denotes that the source and/or drain region is formed on the uppermost surface of the semiconductor substrate 10. The raised source and drain regions typically have the same conductivity type, i.e., n-type or p-type, as the source and drain regions 24, 26. The raised source and drain regions is comprised of an epitaxial semiconductor material that is doped in-situ, or ex-situ by one of ion implantation, or gas phase doping.

Epitaxially growing, epitaxial growth and/or deposition" mean the growth of a semiconductor material on a deposition surface of a semiconductor material, in which the semiconductor material being grown has the same crystalline characteristics as the semiconductor material of the deposition surface. In the present embodiment, the semiconductor material that is used in forming the raised source region and the raised drain region has the same crystalline characteristics as that of the physically exposed uppermost surface of the semiconductor substrate 10. When the chemical reactants are controlled and the system parameters set correctly, the depositing atoms arrive at the deposition surface with sufficient energy to move around on the surface and orient themselves to the crystal arrangement of the atoms of the deposition surface. Thus, an epitaxial film deposited on a {100} crystal surface will take on a {100} orientation. In some embodiments, the epitaxial deposition process is a selective deposition process.

The semiconductor material that can be epitaxially deposited and used as the raised source and drain regions includes any semiconductor material such as, for example, silicon (Si), germanium (Ge), and silicon germanium (SiGe). In one embodiment, the semiconductor material used as the raised source and drain regions includes a same semiconductor material as that of the semiconductor substrate 10. In another embodiment, the semiconductor material used as the raised source and drain regions includes a different semiconductor material as that of the semiconductor substrate 10. It is noted that the specific material compositions for the semiconductor material that may be used as raised source and drain regions are provided for illustrative purposes only, and are not intended to limit the present disclosure, as any semiconductor material that may be formed using an epitaxial growth process.

A number of different sources may be used for the deposition of semiconductor material that may be used in forming the raised source and drain regions. In some embodiments, in which the semiconductor material used in forming the raised source and drain regions is composed of silicon, the silicon gas source for epitaxial deposition may be selected from the group consisting of hexachlorodisilane ($Si_2Cl_6$), tetrachlorosilane ($SiCl_4$), dichlorosilane ($Cl_2SiH_2$), trichlorosilane ($Cl_3SiH$), methylsilane (($CH_3$)$SiH_3$), dimethylsilane (($CH_3$)$_2$$SiH_2$), ethylsilane (($CH_3CH_2$)$SiH_3$), methyldisilane (($CH_3$)$Si_2H_5$), dimethyldisilane (($CH_3$)$_2Si_2H_4$), hexamethyldisilane (($CH_3$)$_6Si_2$) and combinations thereof. In some embodiments, in which semiconductor material used in forming the raised source and drain regions is composed of germanium, the germanium gas source for epitaxial deposition may be selected from the group consisting of germane ($GeH_4$), digermane ($Ge_2H_6$), halogermane, dichlorogermane, trichlorogermane, tetrachlorogermane and combinations thereof. In some embodiments, in which the semiconductor material used in forming the raised source and drain regions is composed of silicon germanium, the silicon sources for epitaxial deposition may be selected from the group consisting of silane, disilane, trisilane, tetrasilane, hexachlorodisilane, tetrachlorosilane, dichlorosilane, trichlorosilane, methylsilane, dimethylsilane, ethylsilane, methyldisilane, dimethyldisilane, hexamethyldisilane and combinations thereof, and the germanium gas sources may be selected from the group consisting of germane, digermane, halogermane, dichlorogermane, trichlorogermane, tetrachlorogermane and combinations thereof.

Notwithstanding which type of semiconductor material is used, dopants (p- or n-type) can be added during the epitiaxual growth process or following the epitaxial growth process. The temperature for epitaxial semiconductor deposition typically ranges from 550° C. to 900° C. Although higher temperature typically results in faster deposition, the faster deposition may result in crystal defects and film cracking.

In some other embodiments (also not shown here), a portion of the gate dielectric 20 that extends above the V-shaped opening 18 and subsequently formed raised source and drain regions can be removed. The removal of this portion of the gate dielectric 20 that extends above the V-shaped opening 18 and the subsequently formed raised source and drain regions includes one of the etchants mentioned above.

Figure 7:
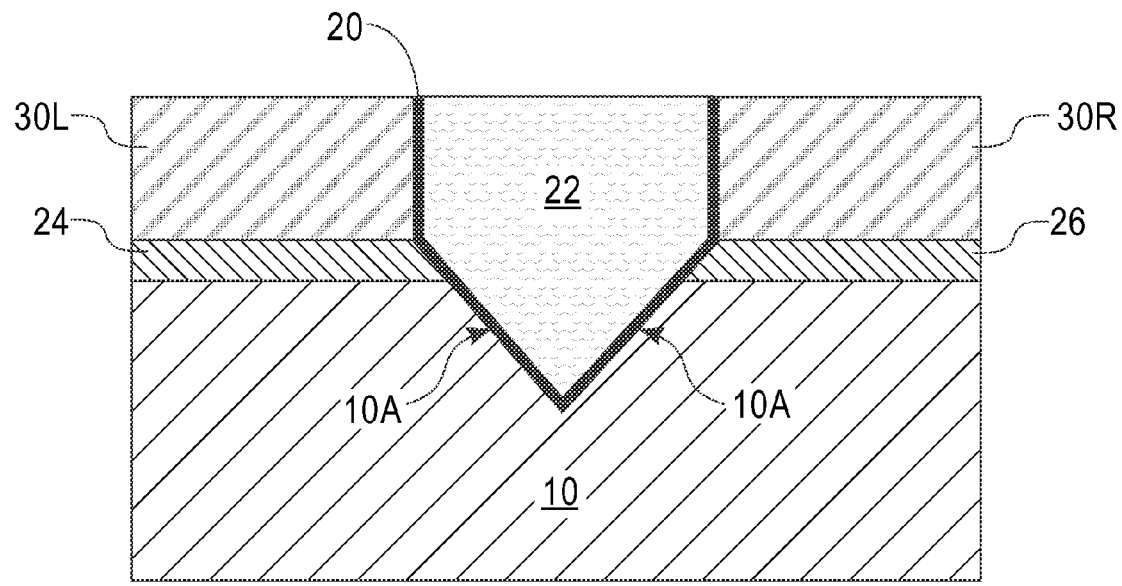
FIG. 7 is a pictorial representation (though a cross sectional view) illustrating the structure of FIG. 6 after forming a first insulator cap portion on an exposed surface of the semiconductor substrate that includes the source region and a second insulator cap portion on an exposed surface of the semiconductor substrate that includes the drain region.

Referring now to FIG. 7, there is illustrated the structure of FIG. 6 after forming a first insulator cap portion 30L on exposed surface of the semiconductor substrate 10 that includes the source region 24 and a second insulator cap portion 30R on exposed surface of the semiconductor substrate 10 that includes the drain region 26. In this embodiment of the present disclosure, the first insulator cap portion 30L is in direct contact with the exposed surface of the semiconductor substrate 10 that includes the source region 24 and the second insulator cap portion 30R is in direct contact with the exposed surface of the semiconductor substrate 10 that includes the drain region 26. In another embodiment not shown here, the first insulator cap portion 30L is in direct contact with the exposed surface of the raised source region and the second insulator cap portion 30R is in direct contact with the exposed surface of the raised drain region.

The first insulator cap portion 30L and the second insulator cap portion 30R are formed by depositing a blanket layer of insulator material on the structure shown in FIG. 6 and then planarizing the blanket layer of insulator material. The blanket layer of insulator material can include one of the insulator materials mentioned above for the blanket layer of hard mask material 12. Also, the blanket layer of insulator material can be formed utilizing one of the techniques mentioned above in forming the blanket layer of hard mask material 12. In one embodiment, the planarization process includes chemical mechanical polishing and/or grinding. In another embodiment, the planarization process includes an etch back process in which a chemical etchant that removes portions of the blanket layer of insulator material selective to the gate dielectric 20 and the sacrificial gate material 22 is employed. At this point of the present disclosure, and as shown in FIG. 7, the uppermost surfaces of the first insulator cap portion 30L and the second insulator cap portion 30R are coplanar with the uppermost surfaces of at gate dielectric 20 and the sacrificial gate material 22.

In some embodiments, and as shown in FIG. 7, the first insulator cap portion 30L has a sidewall surface that directly contacts a portion of the gate dielectric 20 that extends above the V-shaped opening 18 and the second insulator cap portion 30R has a sidewall surface that directly contacts another portion of the gate dielectric 20 that extends above the V-shaped opening 18. In yet another embodiment (now shown here), the first insulator cap portion 30L has a sidewall surface that directly contacts a portion of the sacrificial gate material 22 that extends above the V-shaped opening 18 and the second insulator cap portion 30R has a sidewall surface that directly contacts another portion of the sacrificial gate material that extends above the V-shaped opening 18.

Figure 8:
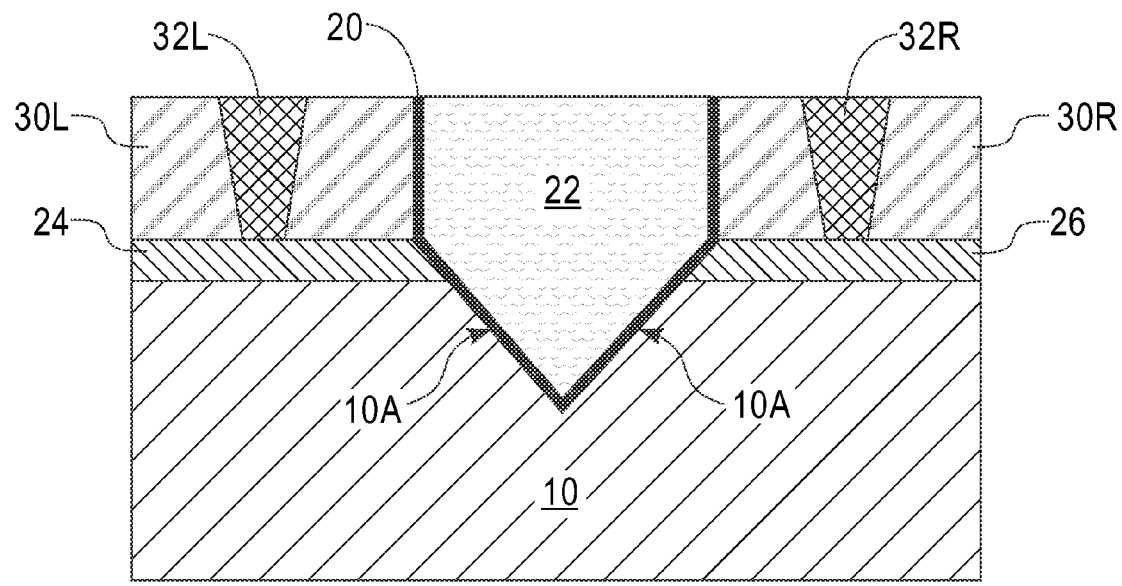
FIG. 8 is a pictorial representation (though a cross sectional view) illustrating the structure of FIG. 7 after forming a first contact to the source region and a second contact to the drain region.

Referring to FIG. 8, there is illustrated the structure of FIG. 7 after forming a first contact, i.e., source contact, 32L to the source region 24 and a second contact, i.e., drain contact, 32R to the drain region 26. The first and second contacts 32L, 32R are formed by first patterning the first and second insulator cap portions 30L, 30R by lithography and etching to include a contact opening in each insulator cap portion 30L, 30R. Etching can be performed by a dry etching process or a wet chemical etching process. In one embodiment of the present disclosure, and when the first and second insulator cap portions 30L, 30R are comprised of silicon oxide, a RIE process comprising $CF_4$ can be used to form the contact openings into each of the first and second insulator cap portions 30L, 30R. In the embodiment illustrated in FIG. 8, the contact opening that is formed into the first insulator cap portion 30L extends to the uppermost surface of the source region 24, while the contact opening that is formed into the second insulator cap portion 30R extends to the uppermost surface of the source region 26.

After the contact openings are formed into each of the first and second insulator cap portions 30L, 30R, the openings are filled with a conductive material including for example, a conductive metal, an alloy comprising at least two conductive metals, a metal silicide or any combination thereof. In one embodiment, the conductive material used to fill each of the contact openings is a conductive metal including, for example, Cu, W or Al. The conductive material can be formed within the contact openings utilizing a deposition process such as, for example, chemical vapor deposition, plasma enhanced chemical vapor deposition, atomic layer deposition, plasma enhanced atomic layer deposition, sputtering chemical solution deposition or plating (electro or electroless). In some embodiments, a planarization process such as chemical mechanical polishing and/or grinding can be used to remove conductive material from atop the upper surface of each of the first and second insulator cap portions 20L, 20R to provide the structure shown in FIG. 8.

Figure 9:
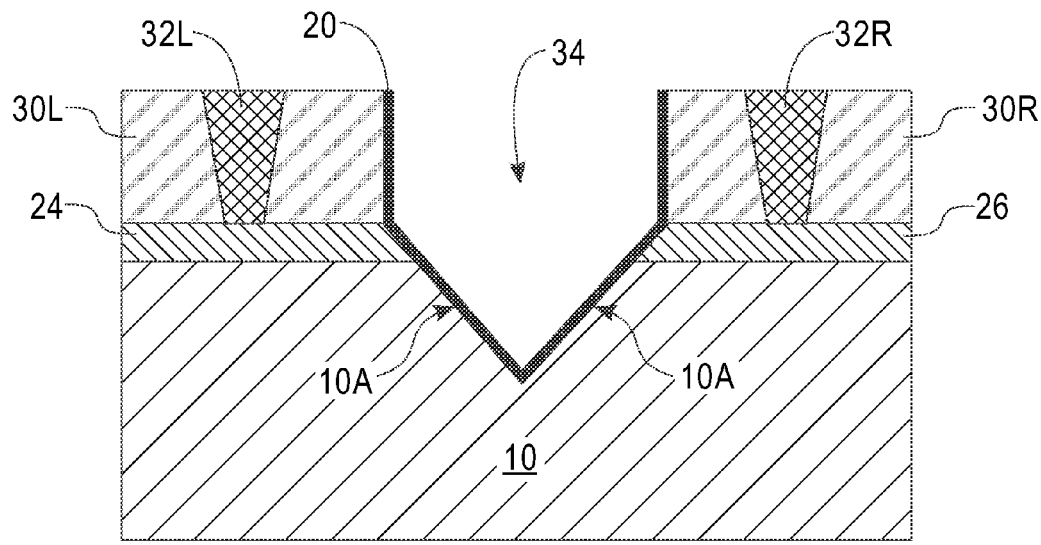
FIG. 9 is a pictorial representation (through a cross sectional view) illustrating the structure of FIG. 8 after removing the entirety of the sacrificial gate material forming a cavity for sensing biomolecules.

Referring now to FIG. 9, there is illustrated the structure of FIG. 8 after removing the entirety of the sacrificial gate material 22 forming a cavity 34 for sensing biomolecules. In this embodiment of the present disclosure, the exposed surfaces 10a that include the V-shaped gate dielectric material portion of gate dielectric 20 serve as a channel region of the structure. The cavity 34 exposes surface of the gate dielectric 20 that are at least present on surfaces 10A of the semiconductor substrate 10 within the V-shaped opening 18. The sacrificial gate material 22 can be removed from the structure utilizing an etching process that selectively removes the sacrificial gate material 22 relative to the first insulator cap portion 30L and the second insulator cap portion 30R and the gate dielectric 20. In one embodiment of the present disclosure, an aqueous solution containing ammonia can be used to selectively remove the sacrificial gate material 22 from the structure. In another embodiment of the present disclosure, a chemical dry etch (CDE) can be used to selectively remove the sacrificial gate material 22 from the structure.

Figure 10A:
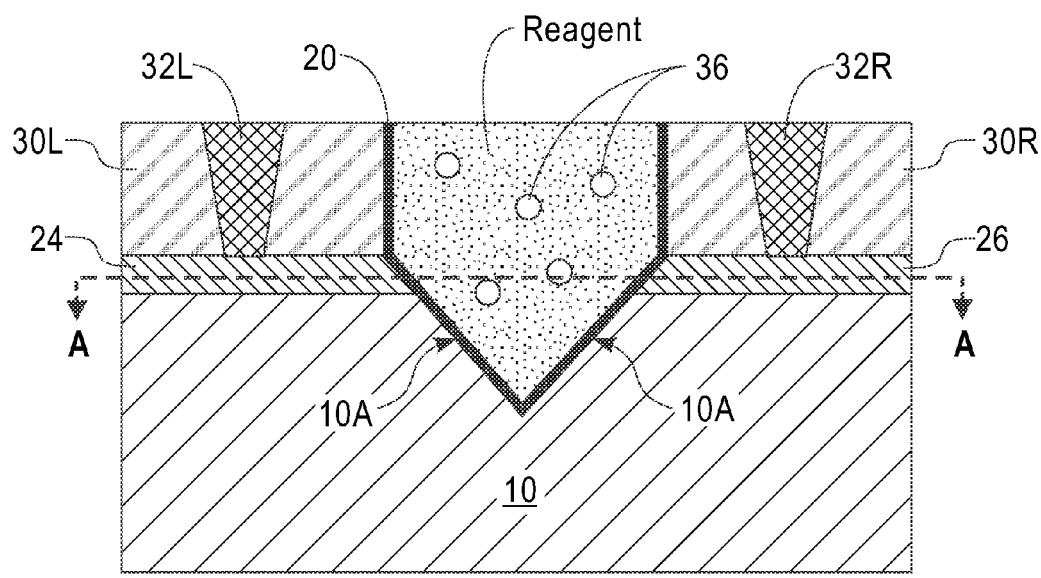
FIG. 10A is a pictorial representation (through a cross sectional view) illustrating the structure of FIG. 9 after providing biomolecules for sensing within the cavity.
Figure 10B:
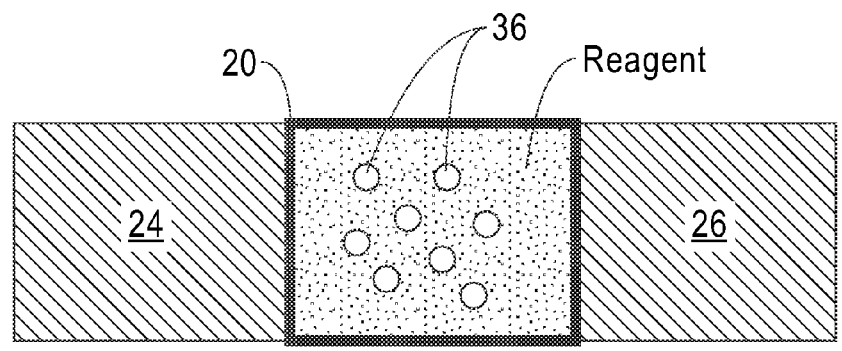
FIG. 10B is a top down view of the structure shown in FIG. 10A through line A-A.

Reference is now made to FIGS. 10A and 10B, which illustrate the structure of FIG. 9 after providing biomolecules 36 for sensing within the cavity 34. The biomolecules 36 are typically present in a reagent or solution such as for example, pH buffer solutions, and phosphate buffer saline (PBS) solutions.

The biomolecules 36 can include any molecule that is produced by a living organism, including large macromolecules such as proteins, polysaccharides, lipids, and nucleic acids, as well as small molecules such as primary metabolites, secondary metabolites, and natural products. In one embodiment, the biomolecules 36 are proteins. Proteins are large biological molecules consisting of one or more chains of amino acids. Proteins perform a vast array of functions within living organisms, including catalyzing metabolic reactions, replicating DNA, responding to stimuli, and transporting molecules from one location to another. Proteins differ from one another primarily in their sequence of amino acids, which is dictated by the nucleotide sequence of their genes, and which usually results in folding of the protein into a specific three-dimensional structure that determines its activity. In another embodiment of the present disclosure, the biomolecules 36 are viruses. A virus is a small infectious agent that can replicate only inside the living cells of an organism. Viruses can infect all types of organisms, from animals and plants to bacteria and archaea.

A field effect transistor (FET) based sensor, such as those described in the present disclosure, may be used to detect biomolecules by measuring the drain current in the subthreshold regime where the drain current has an exponential dependence on the gate voltage of the FET. The sensing principal for FET sensors are discussed in detail in the following references: P. Bergveld, Sensors and Actuators B 88 (2003) 1-20; E. Stern et al, Nature, Vol. 445, page 519 (2007). The sensitivity and response time of the FET sensor depends on the gate dielectric sensing area and this disclosure provides methods for enhancing sensing surface area and thereby enhancing sensitivity.

Figure 11:
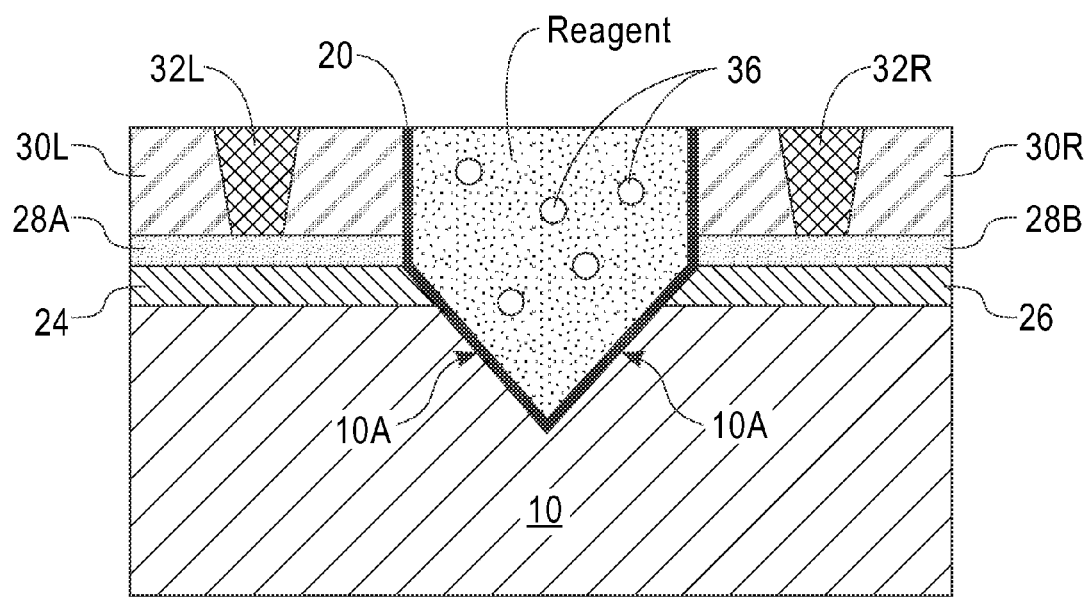
FIG. 11 is a pictorial representation (through a cross sectional view) illustrating another structure that can be formed in the present disclosure for detecting biomolecules.

Reference is now made to FIG. 11, which illustrates a structure that is similar to the structure that is shown in FIG. 10 except that a raised source region 28A and a raised drain region 28B as defined above are present.

Figure 12:
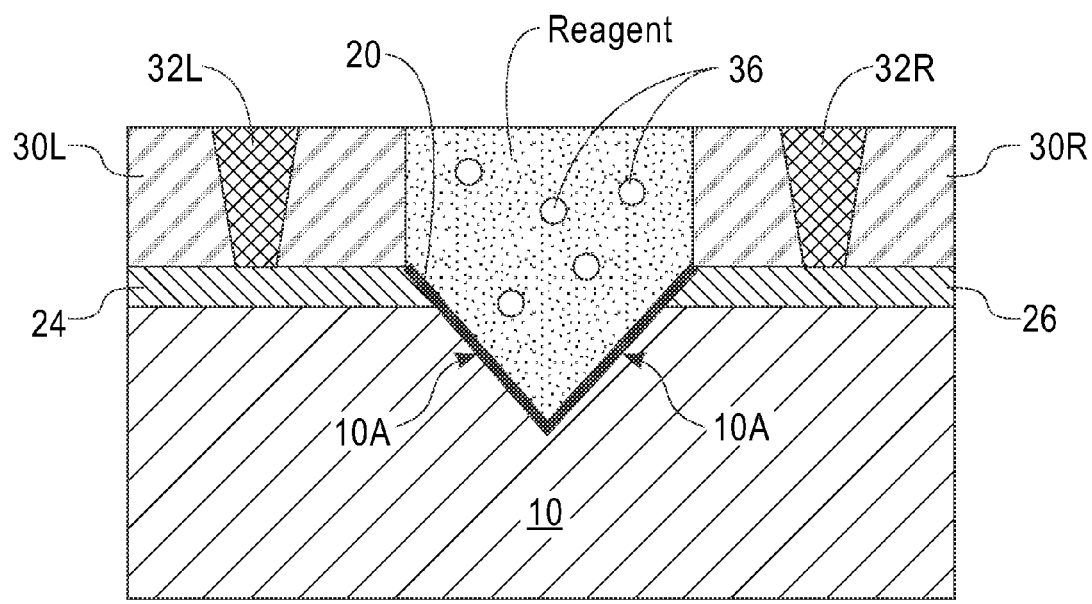
FIG. 12 is a pictorial representation (through a cross sectional view) illustrating yet another structure that can be formed in the present disclosure for detecting biomolecules.

Reference is now made to FIG. 12, which illustrates a structure that is similar to the structure that is formed in FIG. 10A except that a portion of the gate dielectric 20 that extends above the V-shaped opening 18 was removed during processing as also defined above.

FIGS. 10A, 10B, 11 and 12 illustrate a first semiconductor structure of the present disclosure that can be used for sensing biomolecules. The first semiconductor structure includes a semiconductor substrate 10 having a V-shaped opening 18 located therein. The V-shaped opening 18 exposes surfaces 10A of the semiconductor substrate 10 that are located beneath an uppermost surface of the semiconductor substrate 10. A gate dielectric 20 having a bare uppermost surface is located on exposed surfaces 10A of the semiconductor substrate 10 within the V-shaped opening 18. A source region 24 is located in a portion of the uppermost surface of the semiconductor substrate 10 and positioned adjacent one side of the V-shaped opening 18, and a drain region 26 is located in another portion of the uppermost surface of the semiconductor substrate 10 and positioned adjacent to an opposite side of the V-shaped opening 18.

Figure 13:
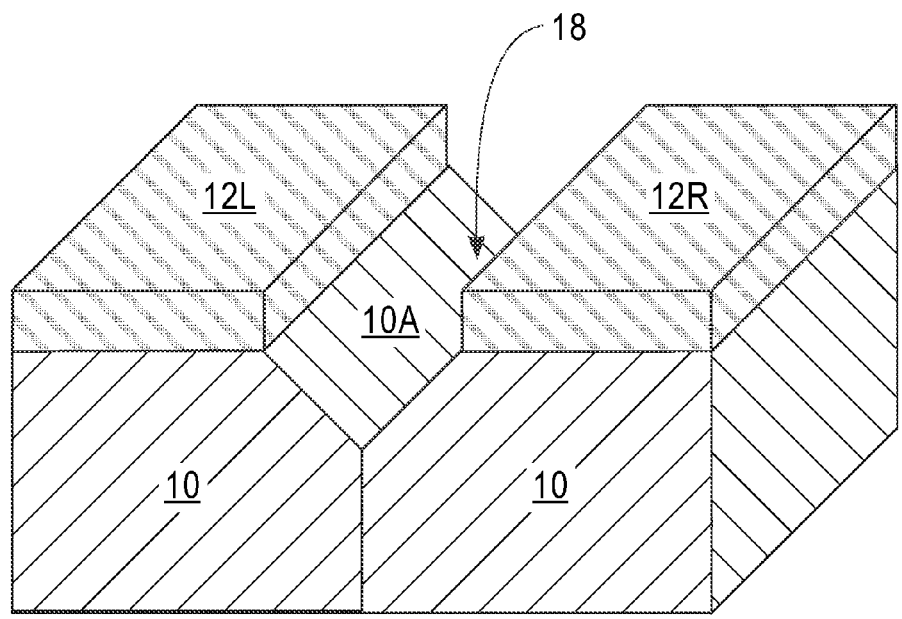
FIG. 13 is a three-dimensional view of the structure shown in FIG. 3 used in accordance with a further embodiment of the present disclosure.

Reference is now made to FIGS. 13-16, which illustrate a yet further embodiment of the present disclosure. This embodiment of the disclosure begins by first providing the structure shown in FIG. 3 of the present disclosure, i.e., a structure including at least one V-shaped opening 18 formed into semiconductor substrate 10 utilizing remaining portions of a blanket layer of hard mask material 12L, 12R that are formed on the semiconductor substrate 10 as an etch mask. A three-dimensional representation of the structure shown in FIG. 3 is illustrated in FIG. 13 of the present disclosure.

Figure 14:
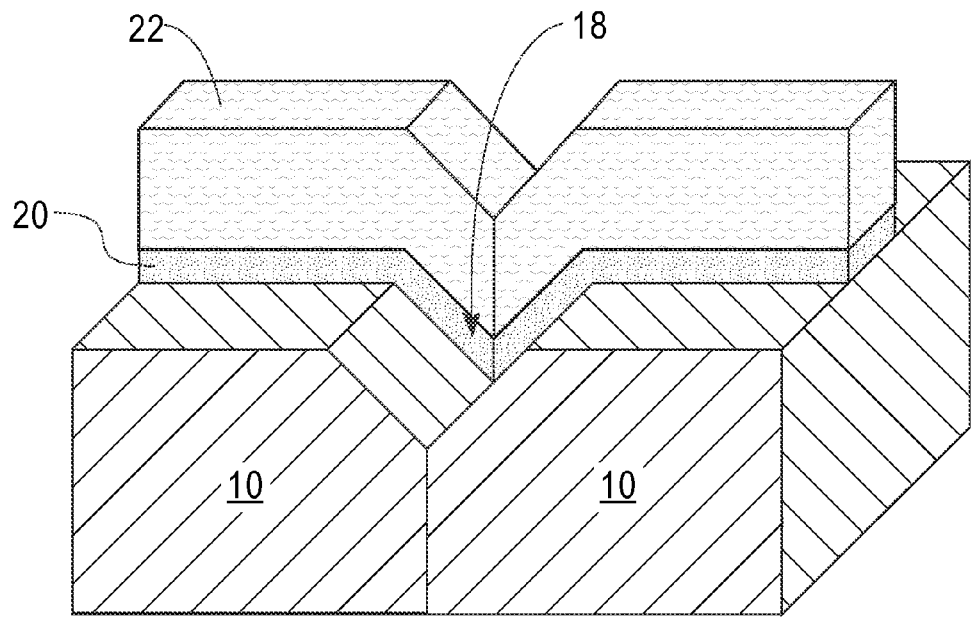
FIG. 14 is a three-dimensional view of the structure shown in FIG. 13 after removing the remaining hard mask material portions from atop the semiconductor substrate and forming a gate dielectric and a sacrificial gate material.

Referring now to FIG. 14, there is illustrated the structure of FIG. 13 after removing the remaining hard mask material portions 12L, 12R from atop the semiconductor substrate 10 and forming a gate dielectric 20 and a sacrificial gate material 22. The removal of the remaining hard mask material portions 12L, 12R from the structure exposes portions of the uppermost surface of the semiconductor substrate 10 that are adjacent the V-shaped opening 18. Unlike the previous embodiment of the present disclosure in which the remaining hard mask material portions 12L, 12R were removed after the gate dielectric 20 and the sacrificial gate dielectric 22 were formed in the V-shaped opening 18, this embodiment of the present disclosure removes the remaining hard mask material portions 12L, 12R prior to forming either the gate dielectric 20 or the sacrificial gate material 22. The removal of the remaining hard mask material portions 12L, 12R from the structure includes an etch that selectively removes the remaining hard mask material portions 12L, 12R relative to the semiconductor substrate 10. In one embodiment of the present disclosure, dilute hydrofluoric acid can be used to remove remaining hard mask material portions 12L, 12R from the structure. In another embodiment of the present disclosure, COR can be used to remove remaining hard mask material portions 12L, 12R from the structure.

Next, a material stack comprising, from bottom to top, a blanket layer of a gate dielectric material and a blanket layer of a sacrificial gate material is formed. The material stack can be formed utilizing the deposition processes mentioned above in forming gate dielectric 20 and the sacrificial gate material 22. The blanket layer of gate dielectric material includes one of the gate dielectric materials mentioned above for gate dielectric 20, while the blanket layer of sacrificial gate material includes one of the sacrificial gate materials mentioned above for sacrificial gate material 22.

A patterning process including lithography and etching is then performed on the blanket layers of gate dielectric material and sacrificial gate material to form at least one patterned structure that includes gate dielectric 20 and sacrificial gate material 22. As shown a portion of the gate dielectric 20 and a portion of the sacrificial gate material 22 are present within the V-shaped opening 18, while other portions of the gate dielectric 20 and the sacrificial gate material 22 are present on the exposed uppermost surface of substrate 10 that is located outside of the V-shaped opening 18. As is also shown, the patterned structure including gate dielectric 20 and the sacrificial gate material 22 runs perpendicular to the direction of the V-shaped opening. As is further shown, the entirety of the exposed surfaces 10A within the V-shaped opening 18 is not covered with gate dielectric material and sacrificial gate material as is the previous embodiment of the present disclosure. Instead, portions of exposed surfaces 10A within the V-shaped opening are bare at this point of the present disclosure.

Figure 15:
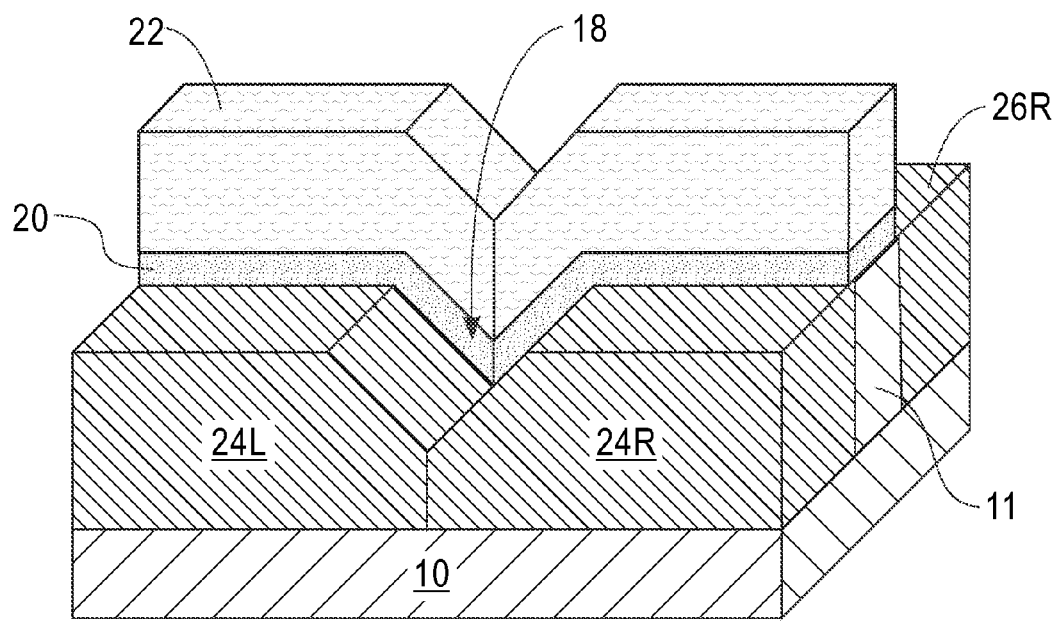
FIG. 15 is a three-dimensional view of the structure shown in FIG. 14 after forming a source region and a drain region in exposed portions of the semiconductor substrate.

Referring now to FIG. 15, there is illustrated the structure of FIG. 14 after forming source regions 24L, 24R in exposed portions of the uppermost surface of the semiconductor substrate 10 on one side of the at least one patterned structure, and drain regions 26L, 26R in exposed portions of the uppermost surface of the semiconductor substrate 10 on the other side of the at least one patterned structure. As shown, an upper portion of the source region 24L is separated from an upper portion of the source region 24R by a portion of the V-shaped opening 18 that does not include the at least one patterned structure. Although not clearly visible in the drawing, an upper portion of the drain region 26L is also separated from an upper portion of the drain region 26R by another portion of the V-shaped opening 18 that does not include the at least one patterned structure. The source and drain regions of this embodiment of the present disclosure can be formed utilizing one of the methods mentioned in forming the source and drain regions in the previous embodiment of the present disclosure. In this embodiment, a channel region 11 is located in the semiconductor substrate 10 and beneath the gate dielectric 20 that is present on the exposed portions of the uppermost surface of the semiconductor substrate.

Figure 16:
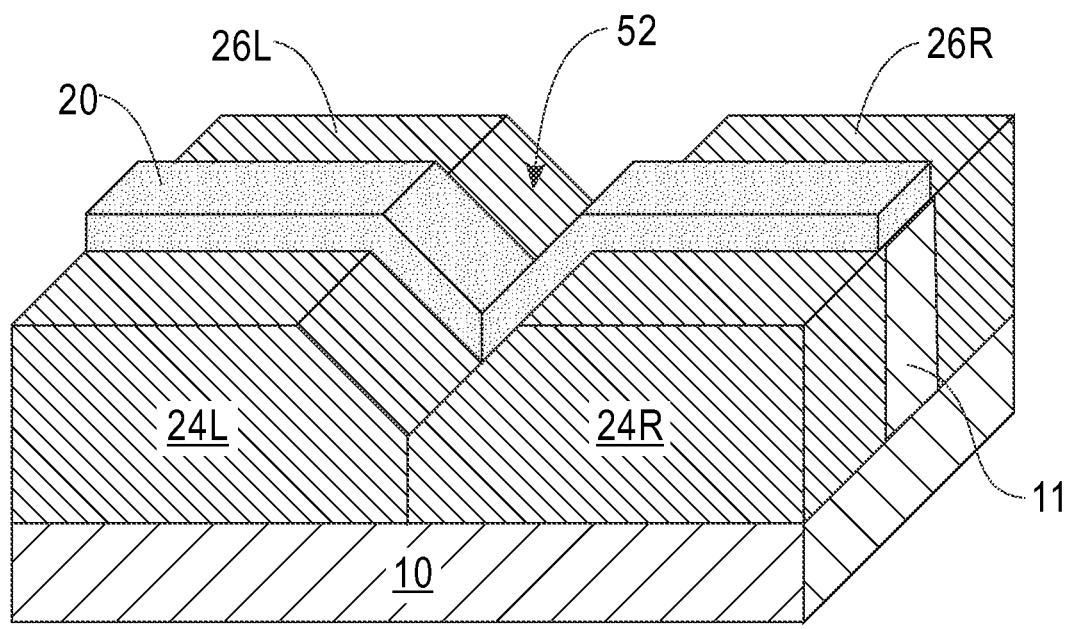
FIG. 16 is a three-dimensional view of the structure shown in FIG. 15 after removing the sacrificial gate material.

Referring now to FIG. 16, there is illustrated the structure of FIG. 15 after removing the sacrificial gate material 22. The sacrificial gate material 22 can be removed utilizing a removal process mentioned above in the previous embodiment of the present disclosure. In this embodiment, biomolecules can be provided into cavity 52 provided by the V-shaped opening 18. Notably, sensing occurs in the area in which gate dielectric 20 is present in the form of a V-shape gate dielectric material portion within cavity 52. More particularly, sensing is performed in this embodiment by applying a gate voltage to the solution and measuring the change in the drain current when the target molecules binds to the gate dielectric sensing surface.

The structure shown in FIG. 16 represents a second semiconductor structure which can be used for sensing biomolecules. This semiconductor structure includes a semiconductor substrate 10 having a V-shaped opening 18 located therein. The V-shaped opening 18 within the semiconductor substrate 10 exposes surfaces 10A of the semiconductor substrate 10 that are located beneath an uppermost surface of the semiconductor substrate 10. A gate dielectric 20 having a bare uppermost surface is located on a portion of the exposed uppermost surface of the semiconductor substrate 10 and on the exposed surfaces 10A of the semiconductor substrate 10 within a portion of the V-shaped opening 18. A source region 24L, 24R is located in exposed portions of the uppermost surface of the semiconductor substrate 10 and positioned adjacent one side of the gate dielectric 20, and a drain region 26L, 26L is located in another exposed portion of the uppermost surface of the semiconductor substrate 10 and positioned on another side of the gate dielectric 20.

While the present disclosure has been particularly shown and described with respect to preferred embodiments thereof, it will be understood by those skilled in the art that the foregoing and other changes in forms and details may be made without departing from the spirit and scope of the present disclosure. It is therefore intended that the present disclosure not be limited to the exact forms and details described and illustrated, but fall within the scope of the appended claims.

What is claimed is:

1. A semiconductor structure for sensing biomolecules, said semiconductor structure comprising:

a semiconductor substrate having a V-shaped opening that extends only partially through said semiconductor substrate and exposes semiconductor material surfaces of the semiconductor substrate that are located beneath an uppermost surface of the semiconductor substrate;

a source region located in a portion of the uppermost surface of the semiconductor substrate and positioned adjacent one side of the V-shaped opening;

a drain region located in another portion of the uppermost surface of the semiconductor substrate and positioned adjacent an opposite side of the V-shaped opening; and a gate dielectric having an entirely bare uppermost surface and being continuously present in said V-shaped opening, wherein said gate dielectric has a bottommost surface portion in direct physical contact with said exposed semiconductor material surfaces of the semiconductor substrate and another bottommost surface portion in direct physical contact with sidewall surfaces, but not topmost surfaces, of both said source region and said drain region.

2. The semiconductor structure of claim 1, further comprising an insulator cap portion located directly on the source region and another insulator cap portion located directly on the drain region.

3. The semiconductor structure of claim 2, wherein said gate dielectric is continuously present on the exposed semiconductor material surfaces of the semiconductor substrate within said V-shaped opening and exposed sidewalls of each insulator cap portion.

4. The semiconductor structure of claim 2, wherein a portion of said gate dielectric material is in direct physical contact with sidewall surfaces of said insulator cap portion and said another insulator cap portion, and wherein a topmost surface of said gate dielectric is coplanar with a topmost surface of both said insulator cap portion and said another insulator cap portion.

5. The semiconductor structure of claim 2, wherein a topmost surface of said gate dielectric is coplanar with a topmost surface of both said source region and said drain region.

6. The semiconductor structure of claim 2, wherein a source contact is present in said insulator cap portion and has a bottommost surface in direct contact with said source region, and a drain contact is present in said another insulator cap portion and has a bottommost surface in direct contact with said source region.

7. The semiconductor structure of claim 6, wherein a topmost surface both said source contact and said drain contact are coplanar with a topmost surface of said gate dielectric.

8. The semiconductor structure of claim 1, further comprising a raised source region located directly on the source region and a raised drain region located directly on the drain region.

9. The semiconductor structure of claim 1, wherein said gate dielectric comprises a dielectric material having a dielectric constant of greater than silicon oxide.

10. The semiconductor structure of claim 1, wherein biomolecules are located within said V-shaped opening and contact a portion of said gate dielectric.

11. The semiconductor structure of claim 1, wherein a channel region is located in said semiconductor substrate and beneath said gate dielectric that is present on the exposed semiconductor material surfaces of the semiconductor substrate within said V-shaped opening.

12. A semiconductor structure for sensing biomolecules, said semiconductor structure comprising:

a semiconductor substrate having a V-shaped opening that extends only partially through said semiconductor substrate and exposes semiconductor material surfaces of the semiconductor substrate that are located beneath an uppermost surface of the semiconductor substrate;

a gate dielectric having an entirely bare uppermost surface located on a portion of the exposed uppermost surface of the semiconductor substrate and having a bottommost surface portion that is in direct physical contact with an entirety of the exposed semiconductor material surfaces of the semiconductor substrate within a portion of the V-shaped opening and other bottommost surface portions that are in directly physical contact with said uppermost surface of said semiconductor substrate on each side of the V-shaped opening;

a source region located in exposed portions of the uppermost surface of the semiconductor substrate and positioned on one side of the gate dielectric and having a bare uppermost surface; and a drain region located in another exposed portion of the uppermost surface of the semiconductor substrate and positioned on another side of the gate dielectric and having a bare uppermost surface.

13. The semiconductor structure of claim 12, wherein said gate dielectric comprises a dielectric material having a dielectric constant of greater than silicon oxide.

14. The semiconductor structure of claim 12, wherein biomolecules are located within said V-shaped opening and contact a portion of said gate dielectric.

15. The semiconductor structure of claim 12, wherein said source region comprises a first portion and a second portion that are separated by said V-shaped opening, and said drain region comprises a first portion and a second portion that are separated by said V-shaped opening.

16. The semiconductor structure of claim 13, wherein a channel region is located in said semiconductor substrate and beneath said gate dielectric that is present on the exposed portions of the uppermost surface of the semiconductor substrate.

* * * * *